US008868226B2

(12) United States Patent
Lal (10) Patent No.: US 8,868,226 B2
(45) Date of Patent: *Oct. 21, 2014

(54) SYSTEMS, METHODS AND APPARATUS FOR FABRICATING AN ORTHOPEDIC IMPLANT

(75) Inventor: Rakesh Lal, Irving, TX (US)

(73) Assignee: Rakesh M. Lal, Medford, MA (US)

( * ) Notice: Subject to any disclaimer, the term of this patent is extended or adjusted under 35 U.S.C. 154(b) by 258 days.

This patent is subject to a terminal disclaimer.

(21) Appl. No.: 12/800,630

(22) Filed: May 19, 2010

(65) Prior Publication Data

US 2011/0288640 A1 Nov. 24, 2011

(51) Int. Cl.
- G06F 19/00 (2011.01)
- A61B 17/80 (2006.01)
- A61L 2/10 (2006.01)
- A61L 2/07 (2006.01)
- A61B 17/00 (2006.01)

(52) U.S. Cl.
CPC ............ *A61B 17/80* (2013.01); *A61L 2202/21* (2013.01); *A61L 2/10* (2013.01); *A61B 2017/00526* (2013.01); *A61L 2/07* (2013.01)
USPC ............................................ 700/119; 600/24

(58) Field of Classification Search
USPC .................. 700/119, 200; 600/24; 409/79, 84
See application file for complete search history.

(56) References Cited

U.S. PATENT DOCUMENTS

| | | | |
|---|---|---|---|
| 5,133,757 A * | 7/1992 | Sioshansi et al. | 128/898 |
| 5,364,602 A | 11/1994 | Leduc | |
| 5,424,047 A | 6/1995 | Zwingenberger et al. | |
| 7,270,592 B2 * | 9/2007 | Duncan et al. | 451/6 |
| 8,017,074 B2 * | 9/2011 | Arnold et al. | 422/33 |
| 8,052,743 B2 * | 11/2011 | Weber et al. | 623/1.38 |
| 2003/0187586 A1 * | 10/2003 | Katzenmaier et al. | 702/19 |
| 2007/0014686 A1 * | 1/2007 | Arnold et al. | 422/28 |
| 2007/0122305 A1 | 5/2007 | Lambert et al. | |
| 2008/0131479 A1 * | 6/2008 | Weber et al. | 424/426 |
| 2008/0257363 A1 | 10/2008 | Schoenefeld et al. | |
| 2009/0131989 A1 | 5/2009 | Willert et al. | |
| 2009/0151736 A1 | 6/2009 | Belcher et al. | |
| 2009/0254093 A1 | 10/2009 | White et al. | |
| 2009/0292363 A1 * | 11/2009 | Goldfarb et al. | 623/17.16 |
| 2010/0217270 A1 * | 8/2010 | Polinski et al. | 606/87 |

OTHER PUBLICATIONS

Taylor eltal., An imagee Diresed Robtic System for Precise Orthopeadic Surgery, Jun. 1994, IEEE Transaction on Robotics and Automation, vol. 10, No. 3, p. 261-275.*
Armand et al., Computer-Aided Orthopedic Surgery with Near-Real Time Biomechanical Feedback, 2004, Johns hopkins APL Techinical Digest., vol. 25, No. 3, p. 242-249.*

* cited by examiner

*Primary Examiner* — Kidest Bahta (57) ABSTRACT

Systems, methods and apparatus are provided through which in some aspects a custom orthopedic implant is designed, fabricated and sterilized for immediate surgical use to treat a patient's injury. In some aspects, the orthopedic implant is designed using patient and injury specific scan data, fabricated using a five axis milling machine, and sterilized with a sterilization system. In other aspects, the fabricated orthopedic implant is transferred into the sterilization system with a transport system. In some aspects, methods to design, fabricate and sterilize a custom orthopedic implant are presented. In other aspects, patient and injury specific scan data is used to design and plan the placement of a custom orthopedic implant to treat the injury, and the custom orthopedic implant is then fabricated and sterilized to be used in surgery.

24 Claims, 7 Drawing Sheets

FIG. 7

SYSTEMS, METHODS AND APPARATUS FOR FABRICATING AN ORTHOPEDIC IMPLANT

FIELD OF THE INVENTION

This invention relates generally to designing and fabricating a patient specific and injury specific orthopedic implant for immediate surgical use, and more particularly to designing and milling an orthopedic implant for immediate surgical use to treat a specific patient's injury, based on a CT scan of the patient's injury.

BACKGROUND OF THE INVENTION

Current processes of treating many orthopedic injuries involve surgically placing orthopedic implants to stabilize, support, compress, or fixate the injury, particularly injuries and fractures to the skeletal system. While some surgical processes are elective, many cases require surgery to be performed immediately, within a few hours of diagnosis. Such cases include emergencies and trauma cases.

Current surgical methods of treating trauma fractures include attaching an elongated plate implant to the bone, using surgical screws and pins at locations proximal and distal to the fracture. The screws are drilled through holes in the plate implant and into healthy bone tissue to ensure the plate is firmly attached to the bone at the site of the fracture.

Trauma implants are usually designed and fabricated off-site before the patient's injury occurs, and a stock of implants is usually stored near the operating room for use in surgical procedures. Since the geometry of both the fracture and the patient's existing anatomy is unknown at fabrication time, the implant may not be optimal for treating a specific patient's injury. To overcome this drawback, implants are usually fabricated in a finite set of shapes and sizes, and are specific to injury type and injury location. Since the variety of injuries and anatomy shapes is very high, a wide range of implants must be fabricated and stored near the operating room. This can result in waste, since many of the implants will never be used. Additionally, some limited customizability is associated with the design of implants. This customizability is usually limited to providing a surgeon with a set of options as to where screws can be placed through the implant. Some implants also permit a surgeon to physically bend the implant along the length of the implant, into a desired shape. While these features add some flexibility to the implant, they are still not customized for a specific patient's injury and may not be optimal to treat the injury.

For the reasons stated above, and for other reasons stated below which will become apparent to those skilled in the art upon reading and understanding the present specification, there is a need in the art for customized orthopedic implants that are immediately available for surgery. There is also a need for improved methods and processes to design, fabricate, and sterilize customized orthopedic implants such that they can be used to surgically treat a patient's injury.

BRIEF DESCRIPTION OF THE INVENTION

The above-mentioned shortcomings, disadvantages and problems are addressed herein, which will be understood by reading and studying the following specification.

In one aspect, a system to fabricate an orthopedic implant for immediate surgical use includes a system to design the three dimensional shape of the orthopedic implant based on patient and injury specific scan data, a fabrication system, a communication link to communicate the three dimensional shape of the orthopedic implant to the fabrication system, and a sterilization system to sterilize the orthopedic implant.

In another aspect, the system to fabricate an orthopedic implant for immediate surgical use further includes a transport system to transfer the orthopedic implant to the sterilization system after fabrication.

In another aspect, a method of fabricating an orthopedic implant for immediate surgical use includes designing the three dimensional shape of the orthopedic implant based on patient and injury specific scan data, communicating the three dimensional shape of the orthopedic implant to a fabrication system, instructing the fabrication system to fabricate the orthopedic implant, and sterilizing the fabricated orthopedic implant.

In yet another aspect, the method of fabricating an orthopedic implant for immediate surgical use further includes mechanically transferring the fabricated orthopedic implant into a sterilization system for sterilization.

In a further aspect, an orthopedic implant is produced by a process that includes designing the three dimensional shape of the orthopedic implant based on patient and injury specific scan data, communicating the three dimensional shape of the orthopedic implant to a fabrication system, instructing the fabrication system to fabricate the orthopedic implant, mechanically transferring the orthopedic implant to a sterilization system, and sterilizing the orthopedic implant.

Apparatus, systems, and methods of varying scope are described herein. In addition to the aspects and advantages described in this summary, further aspects and advantages will become apparent by reference to the drawings and by reading the detailed description that follows.

DETAILED DESCRIPTION OF THE INVENTION

In the following detailed description, reference is made to the accompanying drawings that form a part hereof, and in which is shown by way of illustration specific aspects which may be practiced. These aspects are described in sufficient detail to enable those skilled in the art to practice the aspects, and it is to be understood that other aspects may be utilized and that logical, mechanical, electrical and other changes may be made without departing from the scope of the aspects. The following detailed description is, therefore, not to be taken in a limiting sense.

The detailed description is divided into four sections. In the first section, a system level overview is described. In the second section, apparatus of aspects are described. In the third section, aspects of methods are described. Finally, in the fourth section, a conclusion of the detailed description is provided.

System Level Overview

Figure 1:
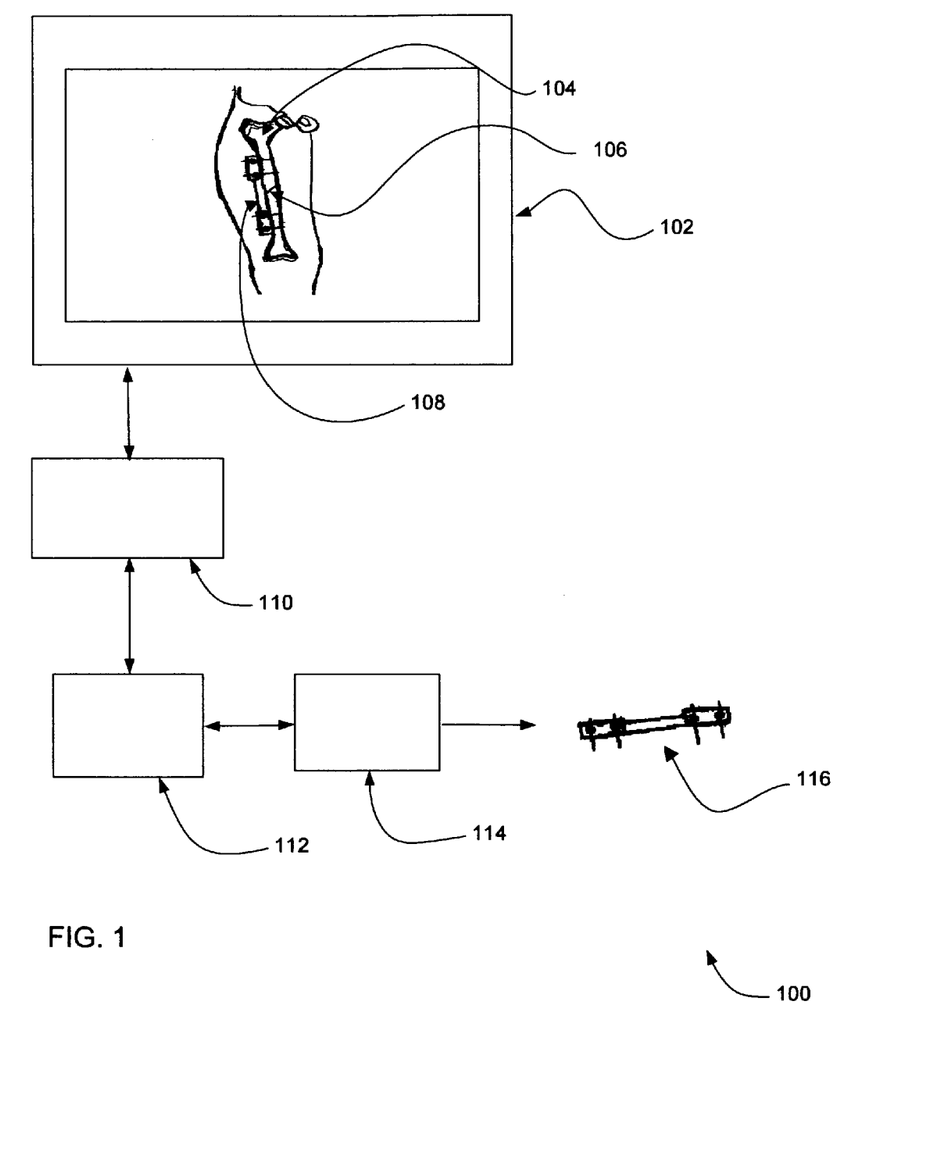
FIG. 1 is a block diagram illustrating the process of visualizing a patient specific injury, designing an orthopedic implant, fabricating the orthopedic implant, and sterilizing the implant.

FIG. 1 is a block diagram illustrating the process of visualizing a patient specific injury, designing an orthopedic implant, fabricating the orthopedic implant, and sterilizing the implant. System 100 solves the need in the art to accurately fabricate and sterilize a custom orthopedic implant designed to treat a specific patient's injury, such that the implant is ready for immediate surgical use.

System 100 includes a visualization system 102 which displays patient scan data 104 and injury scan data 106. System 100 further includes a set of tools to design the three dimensional shape of a custom orthopedic implant 108 to treat the injury. A communication system 110 transmits the three dimensional shape of the custom orthopedic implant to a fabrication system 112 which fabricates the three dimensional shape into a physical object. The physical object is transferred to a sterilization system 114, which produces a sterilized custom orthopedic implant designed to treat a specific patient's injury 116, where the implant is ready for immediate surgical use.

Component 102 solves the need in the art to visualize and design a custom orthopedic implant designed to treat a specific patient's injury based on patient specific and injury specific scan data.

Component 112 solves the need in the art to fabricate a custom orthopedic implant designed to treat a specific patient's injury, based on the 3 dimensional design of the implant.

Component 114 solves the need in the art to sterilize a custom orthopedic implant designed to treat a specific patient's injury, such that the implant is ready for immediate surgical use.

The system level overview of the operation of an aspect is described in this section of the detailed description. The visualization system is used to present a user with a patient specific and injury specific scan data. In some aspects, the visualization system includes a system to design the three dimensional shape of the orthopedic implant based on the patient and injury specific scan data. In other aspects, the visualization system further includes a system to present a user with an initial three dimensional shape, and a system to provide the user with design tools to edit the initial three dimensional shape to form a final three dimension shape. In yet other aspects, the patient specific and injury specific scan data includes a computed tomography scan of the patient's injury site.

The communication system transmits the three dimensional shape of the orthopedic implant to the fabrication system. In some aspects the communication system includes a network cable and a communication protocol to transmit data. In other aspects the communication system includes a wireless transmitter and receiver and a communication protocol.

The fabrication system fabricates the three dimensional shape of the orthopedic implant, and the sterilization system sterilizes the fabricated implant for immediate surgical use. In some aspects the fabrication system includes a subtractive fabrication system such as a five axis milling system. In other aspects, the fabrication system includes an additive fabrication system. In other aspects, the additive fabrication system includes a direct metal laser sintering system. In yet other aspects, the additive fabrication system includes an electron beam melting system. In further aspects, the fabrication system includes both a subtractive fabrication system and an additive fabrication system working in conjunction to form a three dimensional shape.

In some aspects the sterilization system includes a sealed chamber capable of maintaining temperatures of 121 C at high pressures continuously for a period of time greater than 15 minutes. In other aspects the sterilization system includes a sealed chamber with an ultraviolet light source.

While the system 100 is not limited to any particular visualization, fabrication and sterilization system, for sake of clarity a simplified visualization, fabrication and sterilization system are described.

Apparatus Aspects

In the previous section, a system level overview of the operation of an aspect was described. In this section, the particular apparatus of such an aspect are described by reference to a series of diagrams.

Figure 2:
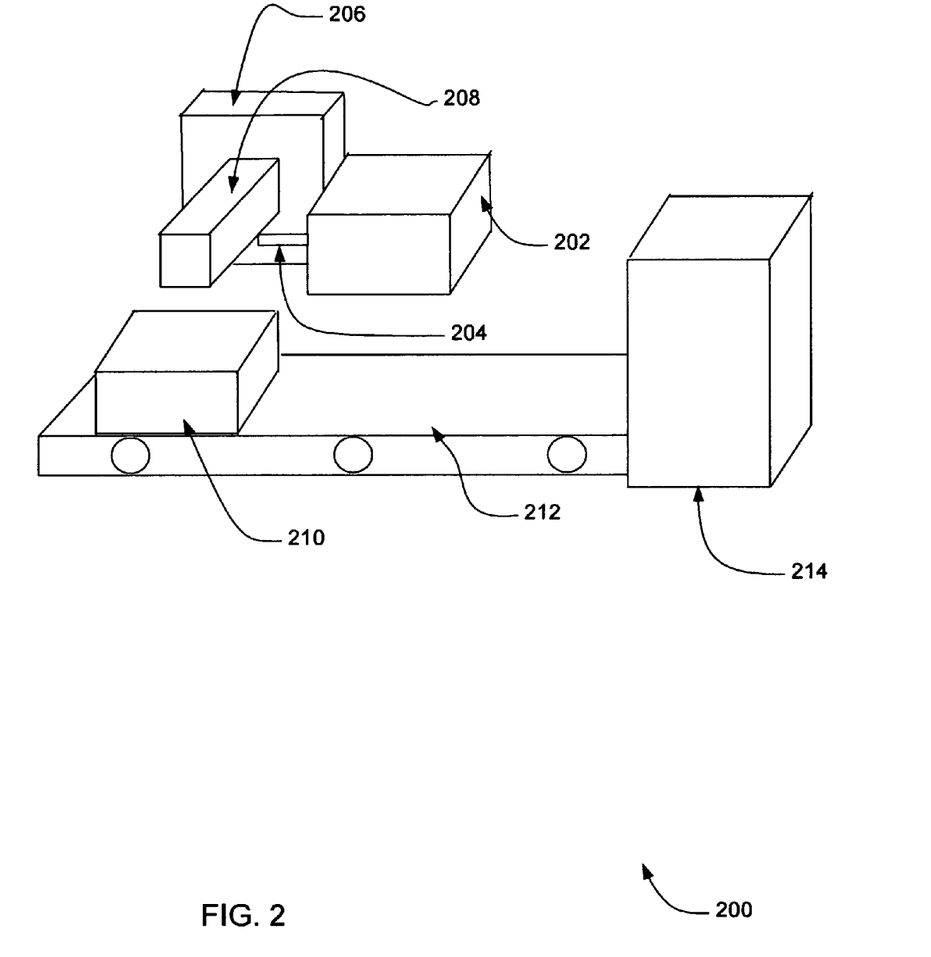
FIG. 2 is a cross section block diagram of an apparatus according to an aspect to accurately and precisely fabricate an orthopedic implant, transport the orthopedic implant, and sterilize the implant.

FIG. 2 is a cross section block diagram of apparatus 200 according to an aspect to accurately and precisely fabricate an orthopedic implant, transport the orthopedic implant, and sterilize the implant. Apparatus 200 solves the need in the art to fabricate an orthopedic implant from a three dimensional shape of the implant, collect the fabricated orthopedic implant, and transport the fabricated orthopedic implant to a sterilization system.

Apparatus 200 includes a carriage 202 which holds a milling tool 204. In some aspects the carriage is capable of independent linear and rotary motion about various axes. In other aspects, the milling tool is connected to the carriage with a spindle that is capable of high speed rotary motion. In yet other aspects, the carriage contains a fluid jet capable to releasing a stream of fluid alongside the milling tool. Apparatus 200 further includes a mill blank holder 206 which holds a mill blank 208. In some aspects the mill blank holder is capable of linear and rotary motion about various axes. Apparatus 200 further includes a collection receptacle 210 to collect the fabricated implant once fabrication is completed, a transport system 212 capable of transporting the fabricated implant into a sterilization system 214. In some aspects the transport system includes a shower system that exposes the fabricated implant to a stream of fluid, and a drainage system to collect and drain fluid released from the fluid jet aspect of the carriage and the shower system. In other aspects, the collection receptacle includes drainage holes that allow drainage of fluid released from the fluid jet of the carriage and the shower system.

Figure 3:
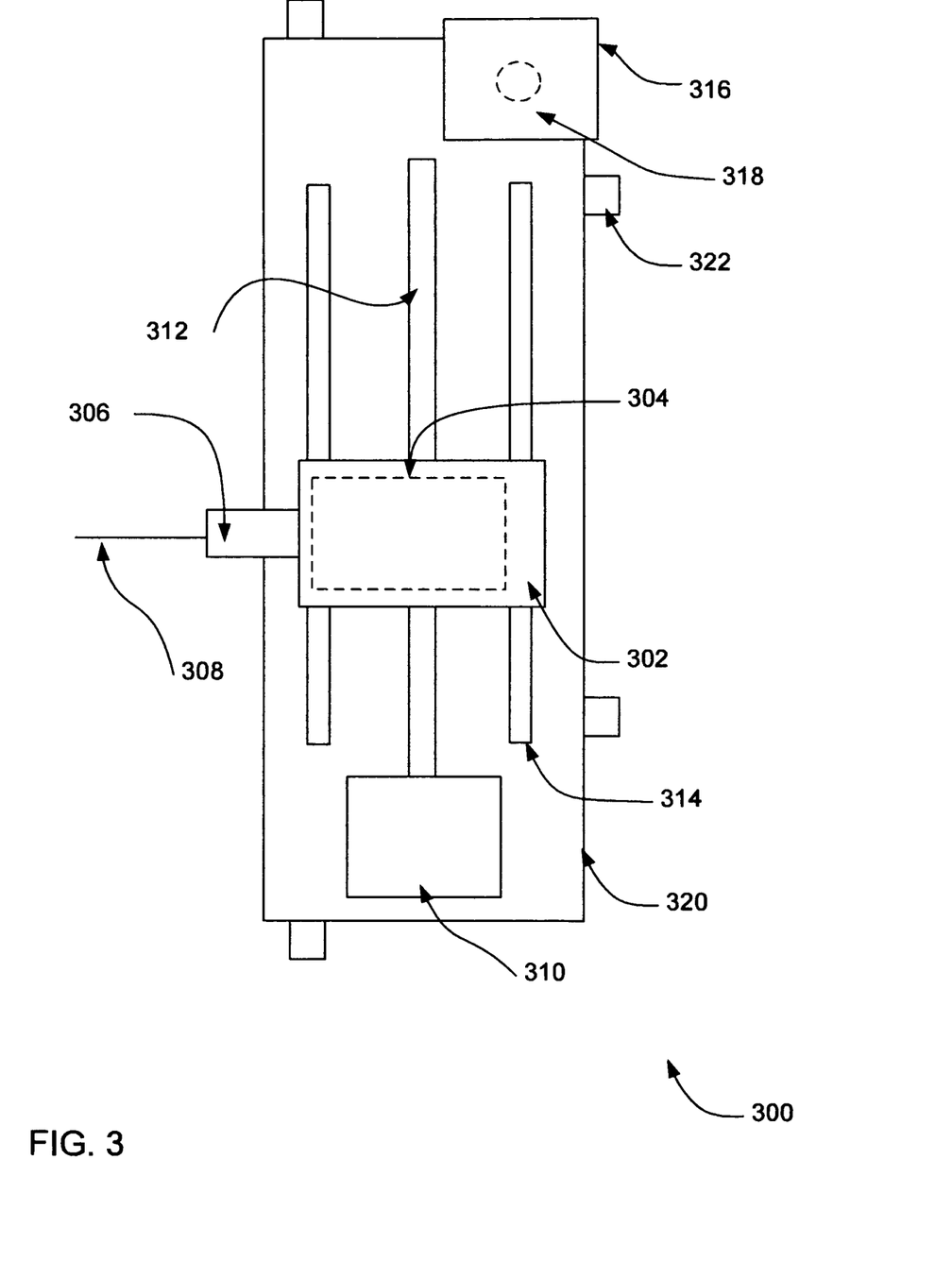
FIG. 3 is a cross section block diagram of an apparatus according to an aspect to accurately and precisely fabricate an orthopedic implant, in which the milling tool system is capable of independent motion in the y-axis and z-axis.

FIG. 3 is a cross section block diagram of apparatus 300 according to an aspect to accurately and precisely fabricate an orthopedic implant, in which the milling tool system is capable of independent motion in the y-axis and z-axis. Apparatus 300 solves the need in the art to impart motion to the milling tool enabling it to fabricate a custom orthopedic implant.

Apparatus 300 includes a carriage 302, a motor 304 embedded within the carnage, a spindle 306 connected to the motor, and a milling tool 308 connected to the spindle. In some aspects, the motor rotates with high velocity causing the spindle to rotate with high velocity, which further causes the milling tool to rotate with high velocity. Apparatus 300 further includes a y-axis motor 310, a y-axis drive shaft 312, and y-axis rails 314. In some aspects, the y-axis drive shaft is connected to the y-axis motor and is capable of rotary motion when the y-axis motor rotates. In other aspects, the y-axis drive shaft is treaded and passes through the carriage so that rotary motion of the y-axis drive shaft causes the carriage to move along the rails.

Apparatus 300 further includes a z-axis motor 316, a z-axis drive shaft 318, a z-axis platform 320, and stabilization pegs 322. In some aspects the carriage and y-axis motor rest on the z-axis platform. In some aspects, the z-axis drive shaft is connected to the z-axis motor and is capable of rotary motion when the z-axis motor rotates. In other aspects, the z-axis drive shaft is treaded and passes through the z-axis platform so that rotary motion of the z-axis drive shaft causes the z-axis platform to move along the z-axis, which in turn causes the carriage to move along the z-axis. In yet other aspects, the stabilization pegs are fixed to the z-axis platform and are also fixed within z-axis rods such that their motion is limited to moving along the z-axis thereby preventing the z-axis platform from wobbling while moving along the z-axis.

Figure 4:
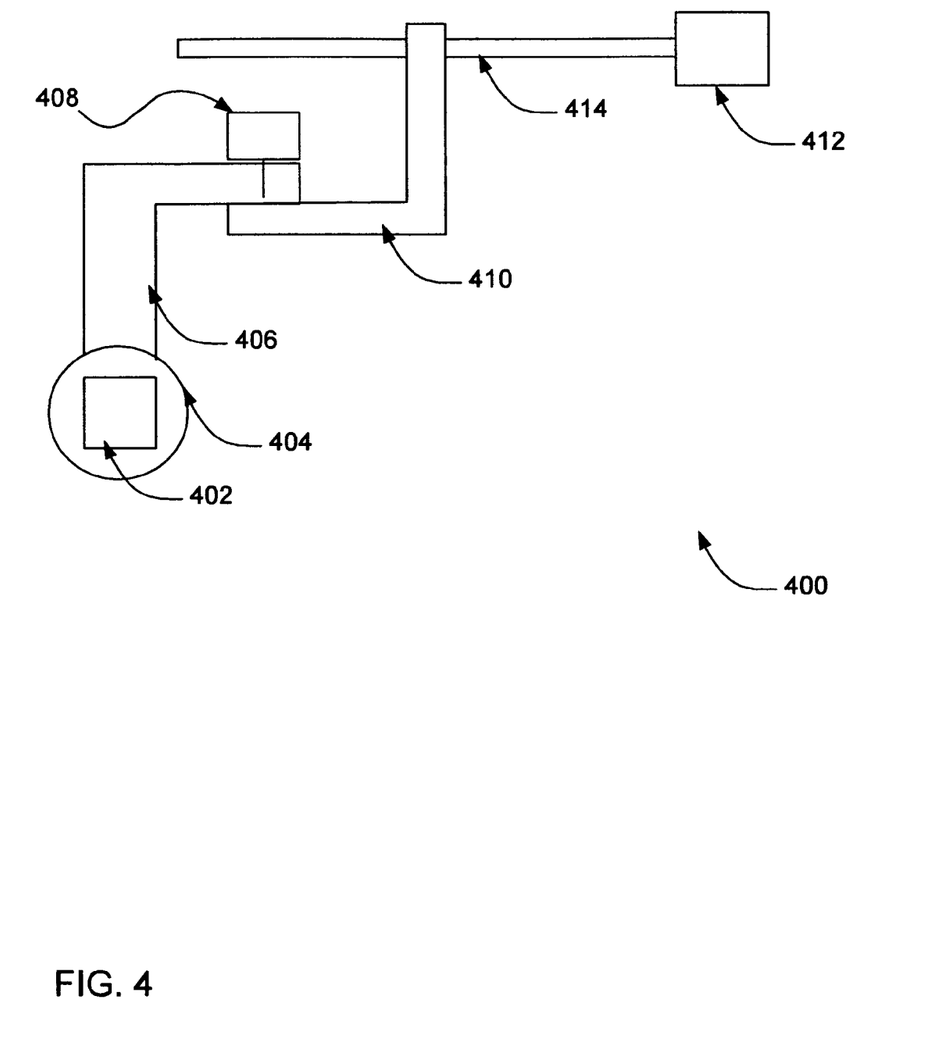
FIG. 4 is a cross section block diagram of an apparatus according to an aspect to accurately and precisely fabricate an orthopedic implant, in which the mill blank holder system is capable of independent rotation about the central axis and longitudinal axis, and linear motion in the x-axis.

FIG. 4 is a cross section block diagram of apparatus 400 according to an aspect to accurately and precisely fabricate an orthopedic implant, in which the mill blank holder system is capable of independent rotation about the central axis and longitudinal axis, and linear motion in the x-axis. Apparatus 400 solves the need in the art to position a mill blank so that it can be fabricated into a custom orthopedic implant by a milling tool.

Apparatus 400 includes a mill blank holder 402, and a central axis motor 404. In some aspects the mill blank holder is connected to the central axis motor and is capable of independent rotary motion about the central axis when the central axis motor rotates. In other aspects, the mill blank holder is connected to the central axis motor by a series of gears to reduce the rotation speed of the mill blank holder and increase the rotational torque.

Apparatus 400 further includes a first longitudinal axis arm 406, a longitudinal axis motor 408, and a second longitudinal axis arm 408. In some aspects the first longitudinal arm is connected to the longitudinal axis motor and is capable of independent rotary motion about the longitudinal axis when the longitudinal axis motor rotates. In other aspects, the first longitudinal arm is connected to the longitudinal axis motor by a series of gears to reduce the rotation speed of the first longitudinal arm and increase the rotational torque. In other aspects, the first longitudinal arm rests on top of the second longitudinal arm, and the second longitudinal arm does not rotate when the longitudinal axis motor rotates.

Apparatus 400 further includes an x-axis motor 412 and an x-axis drive shaft 414. In some aspects, the x-axis drive shaft is connected to the x-axis motor and is capable of rotary motion when the x-axis motor rotates. In other aspects, the x-axis drive shaft is treaded and passes through the second longitudinal arm so that rotary motion of the x-axis drive shaft causes the second longitudinal arm to move along the x-axis.

Figure 5:
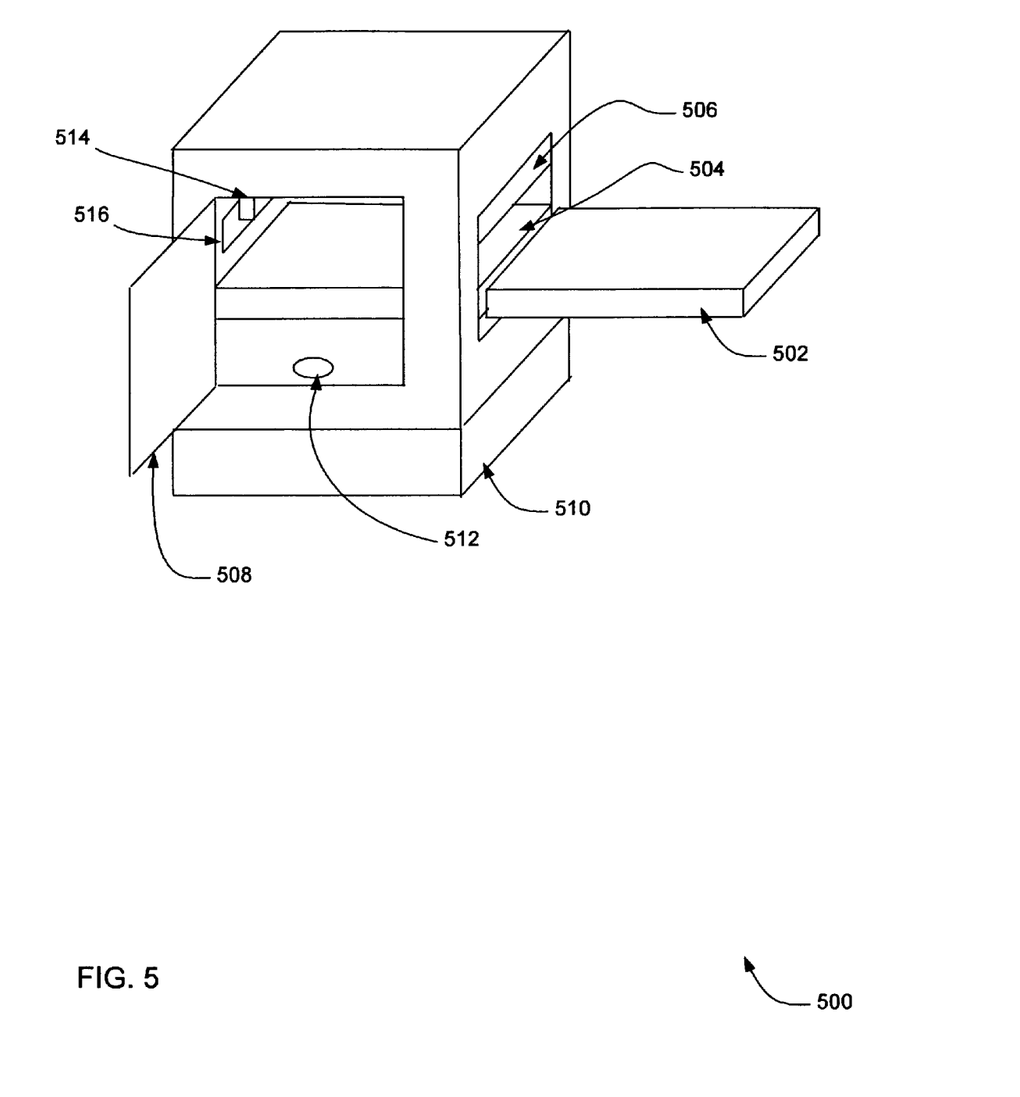
FIG. 5 is a cross section block diagram of an apparatus according to an aspect to sterilize the orthopedic implant, in which a transport system deposits the orthopedic implant into a sterilization chamber, and the implant is sterilized by either exposure to heated steam under high pressure, exposure to ultra-violet light, or both.

FIG. 5 is a cross section block diagram of apparatus 500 according to an aspect to sterilize the orthopedic implant, in which a transport system deposits the orthopedic implant into a sterilization chamber, and the implant is sterilized by either exposure to heated steam under high pressure, exposure to ultra-violet light, or both. Apparatus 500 solves the need in the art to sterilize the fabricated orthopedic implant so that it is ready for surgical use.

Apparatus 500 includes a transport system 502 to transport the fabricated orthopedic implant into the sterilization chamber 504, and a side door 506 that closes to seal the side of the sterilization chamber. In some aspects the fabricated orthopedic implant is contained within a collection receptacle. Apparatus 500 further includes a front door 508 that closes to seal the front of the sterilization chamber, and opens to allow access to the fabricated orthopedic implant.

Apparatus 500 further includes a steam chamber 510 where steam is heated, a steam source 512 that introduces heated steam into the sterilization chamber, and a steam drain 514 that drains steam away from the sterilization chamber. In some aspects the steam is heated to a temperature greater than 121 C and the fabricated orthopedic implant is continuously exposed to the heated steam for a period greater than 15 minutes. Apparatus 500 further includes an ultraviolet light source 516.

Method Aspects

In the previous section, apparatus of the operation of an aspect was described. In this section, the particular methods performed by usage of such an aspect are described by reference to a series of flowcharts.

Figure 6:
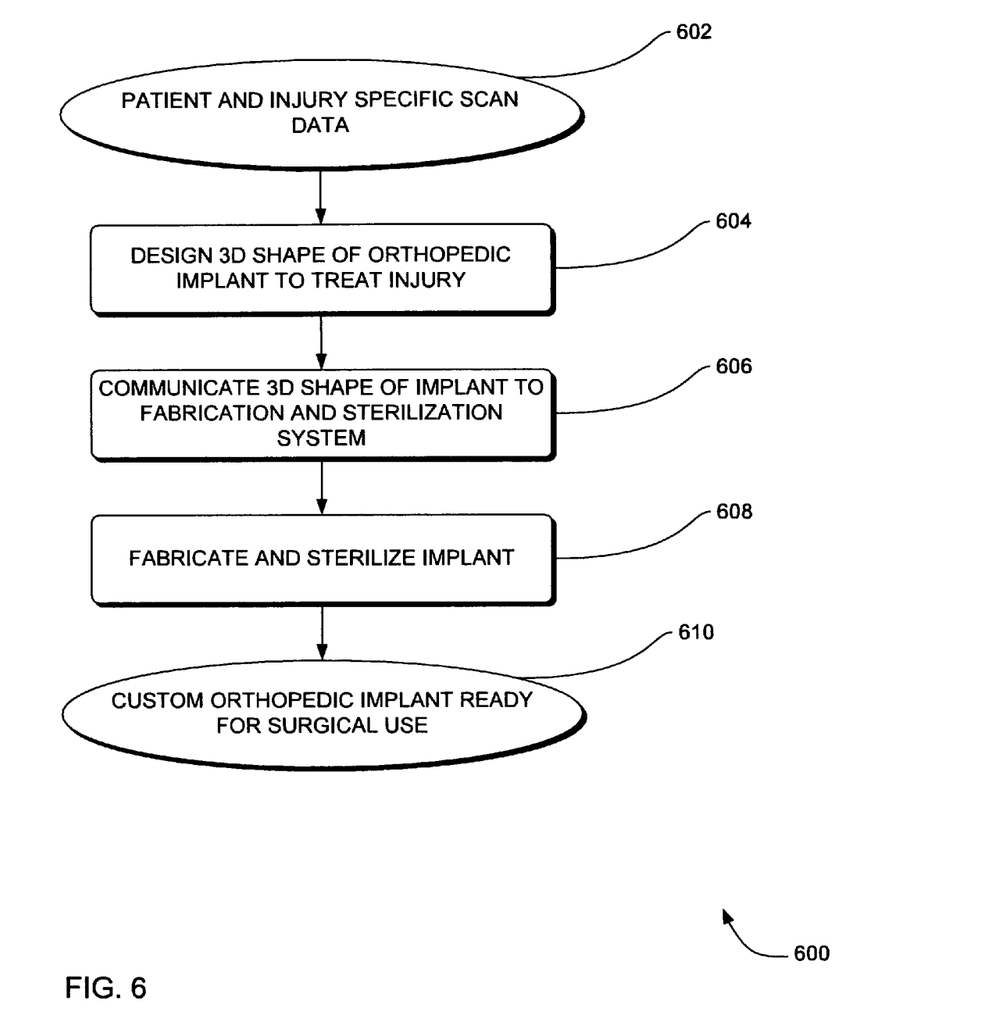
FIG. 6 is a flowchart of a method to design, fabricate and sterilize a custom orthopedic implant such that it is ready for surgery.

FIG. 6 is a flowchart of method 600 to design, fabricate and sterilize a custom orthopedic implant such that it is ready for surgery according to an aspect. Method 600 solves the need in the art to create and sterilize a custom fabricated orthopedic implant designed to treat a specific patient's injury, such that the implant is ready for immediate surgical use.

Method 600 includes patient and injury specific scan data 602, designing the three dimensional shape of an orthopedic implant to treat the injury 604, communicating the three dimensional shape of the orthopedic implant to a fabrication and sterilization system 606, fabricating and sterilizing the fabricated orthopedic implant 608, and yields a custom fabricated orthopedic implant ready for surgical use 610.

In some aspects communicating the three dimensional shape of the orthopedic implant includes communicating an electronic signal representing the three dimensional shape of the orthopedic implant over a network cable, using a communication protocol. In other aspects, communicating the three dimensional shape of the orthopedic implant includes communicating an electronic signal representing the three dimensional shape of the orthopedic implant over a wireless network, using a communication protocol.

In some aspects fabricating the orthopedic implant includes instructing a five axis milling system to fabricate the orthopedic implant. In other aspects, fabricating the orthopedic implant includes a instructing a three dimensional printer to fabricate the orthopedic implant. In yet other aspects, the fabricating the orthopedic implant includes instructing a stereo-lithography system to fabricate the orthopedic implant.

In some aspects, fabricating the orthopedic implant includes mechanically collecting the orthopedic implant after fabrication, and mechanically transferring the orthopedic implant to a sterilization system.

In some aspects sterilizing the fabricated orthopedic implant includes continuously exposing the orthopedic implant to high pressure steam heated to a temperature of 121 C or greater in a sealed chamber for a period of time greater than 15 minutes, and draining the steam away from the orthopedic implant. In other aspects sterilizing the fabricated orthopedic implant includes exposing the orthopedic implant to ultraviolet light.

Figure 7:
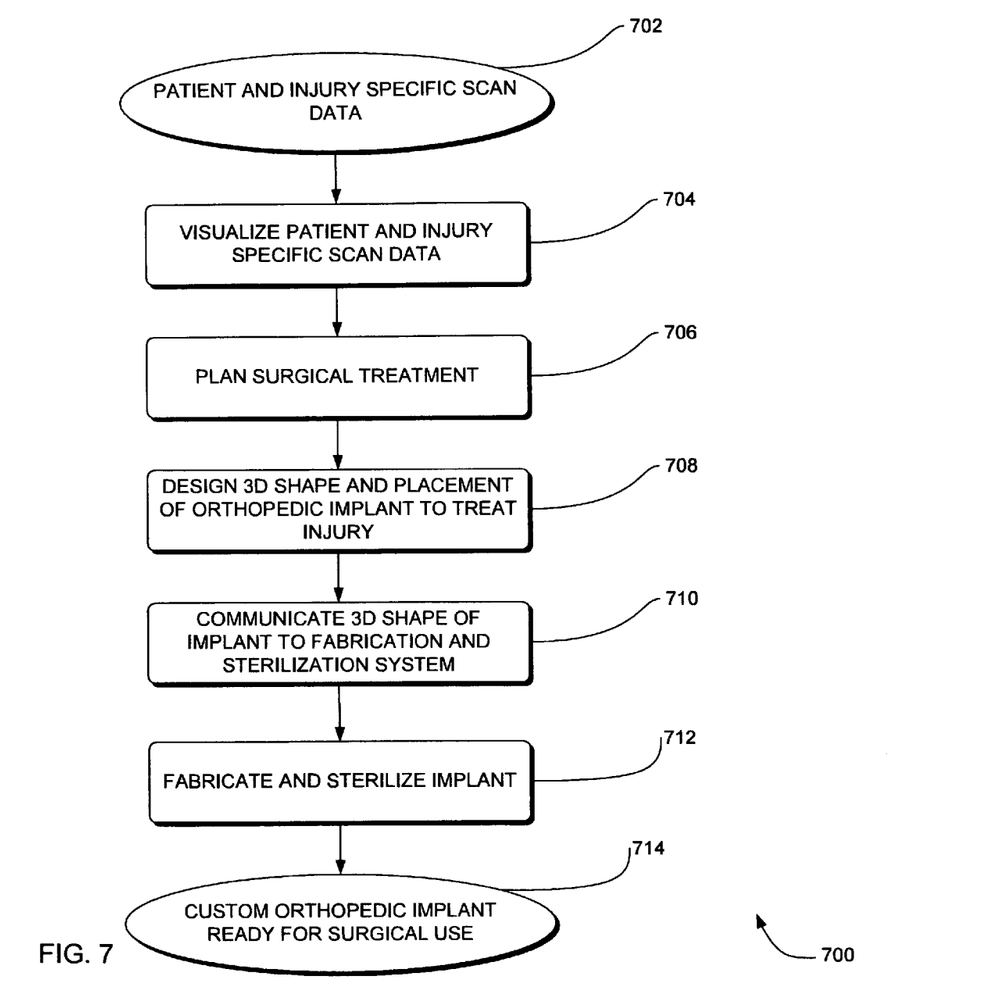
FIG. 7 is a flowchart of a method to plan a surgical treatment involving a custom orthopedic implant, and fabricating and sterilizing the orthopedic implant.

FIG. 7 is a flowchart of method 700 to plan a surgical treatment involving a custom orthopedic implant, and fabricating and sterilizing the orthopedic implant. Method 700 solves the need in the art to design an orthopedic implant to treat a specific patient's injury, and fabricate and sterilize the orthopedic implant, such that the implant is ready for immediate surgical use.

Method 700 includes patient and injury specific scan data 702, visualizing the patient and injury specific scan data 704, planning a surgical treatment to treat the injury 706, designing the three dimensional shape and placement of an orthopedic implant to treat the injury 708, communicating the three dimensional shape of the orthopedic implant to a fabrication and sterilization system 710, fabricating and sterilizing the fabricated orthopedic implant 712, and yields a custom fabricated orthopedic implant designed to treat a specific patient's injury and ready for surgical use 714.

In some aspects designing the three dimensional shape and placement of an orthopedic implant includes presenting a user with an initial three dimensional shape and an initial position of the initial three dimensional shape, providing the user with tools to edit the initial three dimensional shape to form a final three dimensional shape, and providing the user with tools to edit the initial position of the three dimensional shape to form a final position of the three dimensional shape.

In other aspects, the initial and final positions of the three dimensional shape include a spatial location and an orientation vector.

In some aspects visualizing the patient and injury specific scan data includes visualizing a computed tomography scan of a patient's injury.

Conclusion

A system to fabricate an orthopedic implant for immediate surgical use is described. Although specific aspects are illustrated and described herein, it will be appreciated by those of ordinary skill in the art that any arrangement which is calculated to achieve the same purpose may be substituted for the specific aspects shown. This application is intended to cover any adaptations or variations. For example, although described in terms of milling an orthopedic implant, one of ordinary skill in the art will appreciate that implementations can be made using any other fabrication mechanism that provides the required function, including three dimensional printing, stereo-lithography, tooling, or machining. Additionally, although described in orthopedic implant terms, one of ordinary skill in the art will appreciate that implementations can also be made that fabricate and sterilize any surgical implant, such as vascular stents, dental or maxillofacial implants, or other implantable device not requiring electronic components, or specialized, automated assembly.

In particular, one of skill in the art will readily appreciate that the names of the methods and apparatus are not intended to limit aspects. Furthermore, additional methods and apparatus can be added to the components, functions can be rearranged among the components, and new components to correspond to future enhancements and physical devices used in aspects can be introduced without departing from the scope of aspects. One of skill in the art will readily recognize that aspects are applicable to future orthopedic implant fabrication and sterilization devices, different methods of acquiring patient and injury specific scan data, and designing, fabricating and sterilizing orthopedic implants, and new methods of designing, fabricating and sterilizing orthopedic implants.

The terminology used in this application is meant to include all systems to design, fabricate and sterilize orthopedic implants in environments where immediate surgical use is required, and alternate technologies which provide the same functionality as described herein.

What is claimed:

1. A system to fabricate an orthopedic implant, having a three dimensional shape, comprising:
   a system to design the three dimensional shape of the orthopedic implant based on patient and injury specific scan data;
   a fabrication system;
   a sterilization system;
   a collection receptacle operable to receive the orthopedic implant from the fabrication system;
   a transport system operable to mechanically transfer the implant from the fabrication system to the sterilization system; and
   a communication link to communicate the three dimensional shape of the orthopedic implant to the fabrication system.

2. The system of claim 1, wherein the system to design the shape of the orthopedic implant based on patient and injury specific scan data further comprises:
   a system to visualize patient and injury specific scan data;
   a system to design the three dimensional shape of the orthopedic implant based on the patient and injury Specific scan data; and
   a system to determine the placement of the orthopedic implant based on the patient and injury specific scan data.

3. The system of claim 2, wherein the system to design the three dimensional shape of the orthopedic implant based on the patient and injury specific scan data further comprises:
   a system to present a user with an initial three dimensional shape;
   a system to provide the user with tools to edit the initial three dimensional shape to form a final three dimensional shape; and
   a communication link to communicate the final three dimensional shape of the orthopedic implant to the fabrication system.

4. The system of claim 3, wherein the patient and injury specific scan data further comprises:
   computed tomography image data.

5. The system of claim 1, wherein the fabrication system further comprises:
   a subtractive fabrication system that removes material from a fabrication blank to form a final shape.

6. The system of claim 5, wherein the fabrication system further comprises:
   a milling machine for milling blanks into orthopedic implants.

7. The system of claim 6, wherein the milling machine further comprises:
   a carriage capable of independent motion in the y-axis, and z-axis;
   a spindle attached to the carriage, wherein the spindle has a central axis and is capable of independent rotary motion about its own central axis;
   a milling tool attached to the spindle; and
   a mill blank holder capable of holding blanks, wherein the mill blank holder has a central axis and a longitudinal axis, the mill blank holder is capable of independently rotating the mill blank about the central axis and longitudinal axis, and independent motion along the x-axis.

8. The system of claim 1, wherein the transport system further comprises:
a transfer mechanism to transfer the orthopedic implant to the sterilization system.

9. The system of claim 1, wherein the sterilization system further comprises:
a receiving mechanism to receive the orthopedic implant from the transport system; and
a sterilization chamber.

10. The system of claim 9, wherein the sterilization chamber further comprises:
a sealed sterilization chamber;
a mechanism to deliver high pressure steam at a temperature greater than or equal to 121 C; and
a mechanism to drain said steam.

11. The system of claim 9, wherein the sterilization chamber further comprises:
a sealed sterilization chamber; and
an ultra-violet light source.

12. The system of claim 1, wherein the fabrication system further comprises:
an additive fabrication system that adds material to form a final shape.

13. The system of claim 12, wherein the additive fabrication system further comprises:
a direct metal laser sintering system.

14. The system of claim 12, wherein the additive fabrication system further comprises:
an electron beam melting system.

15. The system of claim 1, wherein the fabrication system further comprises:
an additive fabrication system; and
a subtractive fabrication system.

16. A method of fabricating an orthopedic implant comprising:
designing the three dimensional shape of the orthopedic implant based on patient and injury specific scan data;
communicating the three dimensional shape of the orthopedic implant to a fabrication system;
instructing the fabrication system to fabricate the orthopedic implant;
mechanically receiving the orthopedic implant from the fabrication system using a collection receptacle;
mechanically transferring the fabricated orthopedic implant, using a transport system, into a sterilization system; and
sterilizing the fabricated orthopedic implant.

17. The method of claim 16, wherein designing the three dimensional shape of the orthopedic implant based on patient and injury specific scan data further comprises:
visualizing patient and injury specific scan data;
planning a surgical treatment for the injury.

18. The method of claim 17, wherein planning a surgical treatment for the injury comprises:
designing the three dimensional shape and placement of the orthopedic implant based on the patient and injury specific scan data.

19. The method of claim 18, wherein designing the three dimensional shape and placement of the orthopedic implant based on the patient and injury specific scan data further comprises:
presenting a user with an initial three dimensional shape and an initial position of the initial three dimensional shape;
providing the user with tools to edit the initial three dimensional shape to form a final three dimensional shape; and
providing the user with tools to edit the initial position of the three dimensional shape to form a final position of the three dimensional shape.

20. The method of claim 19, wherein the patient and injury specific scan data further comprises:
computed tomography image data.

21. The method of claim 16, wherein instructing the fabrication system to fabricate the orthopedic implant further comprises:
instructing a milling machine to mill a milling blank into an orthopedic implant.

22. The method of claim. 16, wherein sterilizing the fabricated orthopedic further comprises:
exposing the fabricated orthopedic implant to high pressure steam at a temperature greater than or equal to 121 C; and
draining the steam away from the orthopedic implant.

23. The method of claim 16, wherein sterilizing the fabricated orthopedic further comprises:
exposing the fabricated orthopedic implant to ultra-violet light.

24. An orthopedic implant produced by the process comprising:
designing the three dimensional shape of an orthopedic implant based on patient and injury specific scan data;
communicating the three dimensional shape of the orthopedic implant to a fabrication system;
instructing the fabrication system to fabricate the orthopedic implant;
mechanically receiving orthopedic implant from the fabrication system, using a collection receptacle;
mechanically transferring the orthopedic implant, using a transport system, to a sterilization system; and
sterilizing the orthopedic implant.

* * * * *